United States Patent
Huppenthal et al.

(10) Patent No.: US 8,297,151 B1
(45) Date of Patent: Oct. 30, 2012

(54) APPARATUS FOR OPENING AND CLOSING A SPECIMEN VIAL

(76) Inventors: Joseph Huppenthal, Flagstaff, AZ (US); Drew Miller, Flagstaff, AZ (US)

( * ) Notice: Subject to any disclaimer, the term of this patent is extended or adjusted under 35 U.S.C. 154(b) by 238 days.

(21) Appl. No.: 12/687,129

(22) Filed: Jan. 14, 2010

Related U.S. Application Data

(60) Provisional application No. 61/145,521, filed on Jan. 17, 2009.

(51) Int. Cl.
*B67B 7/00* (2006.01)

(52) U.S. Cl. ............. 81/3.2; 81/3.08; 81/3.36; 53/381.4

(58) Field of Classification Search ............ 81/3.2, 81/3.07, 3.08, 3.36, 3.37, 3.55, 3.39
See application file for complete search history.

(56) References Cited

U.S. PATENT DOCUMENTS

| | | | |
|---|---|---|---|
| 2,049,879 A * | 8/1936 | Townsend et al. | 81/3.37 |
| 2,273,583 A * | 2/1942 | Meister | 414/381 |
| 3,125,840 A * | 3/1964 | Cross | 53/157 |
| 3,545,174 A * | 12/1970 | Randrup | 53/381.4 |
| 3,552,090 A * | 1/1971 | Roberts et al. | 53/71 |
| 4,773,285 A * | 9/1988 | Dionne | 81/3.2 |
| 5,255,574 A * | 10/1993 | Wuerschum | 81/3.2 |
| 5,481,946 A * | 1/1996 | Nishikawa et al. | 81/3.2 |
| 6,257,091 B1 * | 7/2001 | Cohen et al. | 81/3.2 |
| 6,866,820 B1 * | 3/2005 | Otto et al. | 422/63 |
| 7,409,809 B1 * | 8/2008 | Degen et al. | 53/381.4 |

\* cited by examiner

*Primary Examiner* — Monica Carter
*Assistant Examiner* — Melanie Alexander
(74) *Attorney, Agent, or Firm* — Coastal Patent Agency; Joshua S. Schoonvoer

(57) ABSTRACT

A lid actuator for opening and closing a specimen vial is provided. The lid actuator is generally adapted for use with automated laboratory equipment, for example, specimen auto sampling equipment, laboratory analytical testing equipment, food and product filling equipment and the like. The lid actuator generally includes an enclosure for maintaining a vial in an upright orientation, and a linkage assembly for rotationally engaging and mechanically opening the lid of the specimen vial. Additional features of the lid-actuator may further include a specimen vial ejection member, a vial catch tray, and an input tray.

17 Claims, 8 Drawing Sheets

APPARATUS FOR OPENING AND CLOSING A SPECIMEN VIAL

CROSS REFERENCE TO RELATED APPLICATIONS

This application is related to Provisional Application Ser. No. 61/145,521 filed Jan. 17, 2009, the entire contents of which are hereby incorporated by reference.

FIELD OF THE INVENTION

This invention relates to an apparatus for opening and closing the lid of a specimen vial. More specifically, this invention relates to an apparatus for use in automated specimen sample processing within a laboratory or other testing location.

BACKGROUND OF THE INVENTION

Many laboratories and other testing facilities are currently available for blood, urine, liquid content, and other specimen testing procedures. Of these, a number of laboratories are testing for the presence of illegal substances, such as, for example, alcohol and drugs, or testing for health related purposes, such as cholesterol or blood sugar levels. Other laboratory tests are also becoming increasingly prevalent in the art.

For many specimen tests, a sample specimen is usually deposited in a sample container by a testable subject at a deposit site, and the sample container containing the specimen sample is delivered to a laboratory for further transfer of an aliquot or other portion of the specimen into a testing vial. The testing vial is then typically introduced into one or more machines for processing and analysis of the specimen.

Because the specimen is transferred into a testing vial, and because the laboratory analysis equipment may test a relatively large number of specimen samples, for example many laboratories test hundreds of specimen samples in a typical day of operation, there remains a concern for cross-contamination and general preservation of sample integrity. For this reason, the specimen collection and analysis field has trended towards automated equipment where feasible.

Additionally, the rapidly increasing costs associated with skilled laborers, and the recent federal tax incentives and other contributing factors have further increased demand for automated laboratory sampling and testing equipment.

One of the most tedious and contamination-susceptible tasks for a laborer to effectuate during a sampling and testing process is the sample container opening and closing protocol. The traditional method for opening and closing a sample container includes providing a laborer wearing gloves, the laborer gripping the sample container with his gloves and manually opening the container using his hands. This time-tested method has been known to result in a high risk for contamination. Often, pressure may build up within the sample container, and upon opening the container, a skilled laborer's glove may come into contact with microscopic spray, spills, or other sample contamination. If the unknowing laborer fails to change gloves, the subsequent sample containers may come into contact with the gloves to yield a cross-contamination. Accordingly, test results may further reflect a false positive and require further confirmation testing.

More recently, mechanical sample opening devices have become available, and the traditional manual opening methods are being replaced. Examples of the prior art lid opening devices are described in U.S. Pat. No. 6,531,096, entitled "METHOD AND APPARATUS FOR AUTOMATICALLY OPENING AND CLOSING VIAL LIDS" by Deveney et. al, hereafter the '096 patent; and U.S. Pat. No. 5,578,494, entitled "CAP ACTUATOR FOR OPENING AND CLOSING A CONTAINER" by Clark et. al, hereafter the '494 patent; the entire contents of which are hereby incorporated by reference.

One limitation with the mechanical sample opening device of the '096 patent includes the power requirements, bulk space, and contamination risk associated with processing a sample container throughout multiple stations. It would be beneficial to provide a lid opening device capable of opening the lid, performing an operation, and closing the lid in a single location. Another limitation with the '096 patent includes the use of pre-scoring elements, which can be sharp and therefore hazardous to the user.

Accordingly, there is a need in the art for an automated sample vial lid-actuator for opening, closing and ejecting a sample vial, the sample vial actuator including a means for opening and closing the lid of a sample vial while preserving the integrity of samples and minimizing contamination risks. The sample vial lid-actuator being further capable of efficient receipt and ejection of sample vials, and processing each sample vial in a single location for further minimizing the risk of contamination.

SUMMARY OF THE INVENTION

It is therefore an object of the present invention to provide an improved apparatus for opening, closing and ejecting a vial, the apparatus adapted for use with automated laboratory sampling and testing equipment, product filling equipment, and other automated processing equipment. The apparatus generally includes a base; a vial alignment member extending vertically from the base; a tab engagement member for one or more of: aligning a vial, engaging a hinged tab, or engaging a rim tab; a motor, such as a stepper motor or servo motor; and a linkage for connecting the motor to the tab engagement member, wherein the linkage is adapted to provide an amount of force sufficient to open the lid of a vial.

In certain embodiments, the apparatus is capable of: engaging a hinged tab of a sample vial; removing the hinged tab from a vial post to unlock the vial lid; using a linkage to rotationally open the lid to an open position where an operation can be performed; closing the lid of the vial; and re-engaging the hinged tab with a vial post to securely close the lid of the sample vial. In another embodiment, the apparatus is capable of: engaging the lid of a saliva vial having a rim tab; using a linkage to rotationally open the lid to an open position where an operation can be performed; and closing the lid of the saliva vial.

In one embodiment, an apparatus is provided according to the general description above, the linkage further includes a first linkage member attached to a second linkage member at a first joint, the first linkage member is further attached to and engaged with the motor. The second linkage member provides leverage for disengaging a hinged tab from a vial post and is fixedly attached to a tab engagement member. The second linkage is additionally connected to a third linkage member at a second joint; the third linkage member is also referred to herein as a lid support member. In this embodiment, the motor is configured to rotationally translate the linkage and tab engagement member such that the hinged tab is rotationally disengaged from the vial post in an upward rotational motion. The tab engagement member and lid support member guide the lid of the vial in a rotational movement until the lid is disposed in an open position. In a similar motion, the motor can rotate in a reverse direction to close the lid and re-engage the hinged tab with the vial post to lock the vial lid in a closed position.

In another embodiment, the apparatus, also referred to as a lid-actuator, further includes an ejection member including an elongated rod. The elongated rod can be adapted to eject a sample vial upon a horizontal translation of the elongated rod, wherein the rod penetrates the lid-opening apparatus through an aperture to engage an enclosed vial, and further translates to eject the vial from the lid-opening apparatus and into a catch tray. The elongated rod can be configured using a rack and pinion type engagement, a hydraulic, pneumatic or other pressure-driven engagement, or the like. In this embodiment, a sample vial can be opened using the lid-actuator, an operation performed within the vial, the vial closed by the lid-actuator, and the vial ejected by the ejection member before a subsequent vial is loaded into the lid-actuator.

In another embodiment, the ejection member can include a linear pneumatic actuator, linear servomotor, manually operated guide, retractable linkage, jointing arm, or the like for advancing the ejection member to eject the vial into the catch tray.

In another embodiment, the lid-actuator is adapted to receive, process, and eject a plurality of sample vials, for example using one or more trays or other members for maintaining the sample vials in an upright position. A spring member can be used to further maintain the plurality of sample vials in a preloaded upright position for high-throughput auto sampling.

In another embodiment, the lid-actuator apparatus further includes a manual actuation member for providing a means to actuate the apparatus in the event of power loss, motor malfunction, or simply where access to power is not readily available.

In another embodiment, the lid-actuator includes one or more apertures for exposing a barcode, or other label, for scanning the sample identification. In this embodiment, the aperture can be positioned on any side or the top of a vial.

Other embodiments and features of the invention will become apparent to one having skill in the art upon review of the detailed description and the attached drawings.

BRIEF DESCRIPTION OF THE DRAWINGS

These and other attributes of the invention are further described in the following detailed description of the invention, particularly when reviewed in conjunction with the drawings, wherein.

DETAILED DESCRIPTION

Figure 1A:
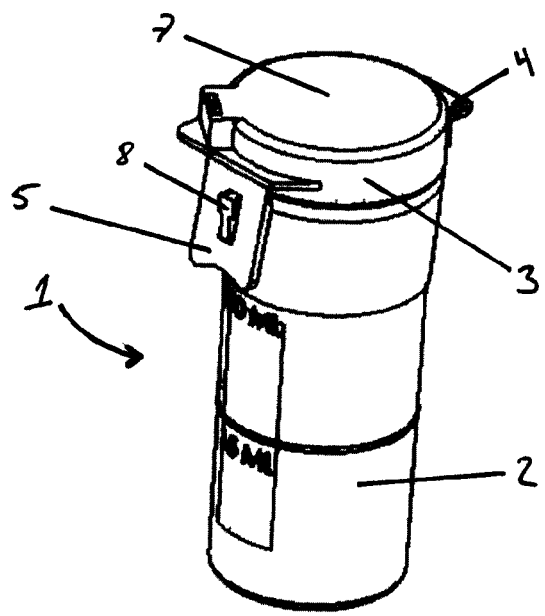
FIGS. 1 (*a-b*) illustrate a perspective view of a typical specimen vial having a container body, a hinged lid, a hinged tab and a vial post.

In the following description, for purposes of explanation and not limitation, details and descriptions are set forth in order to provide a thorough understanding of the present invention. However, it will be apparent to those skilled in the art that the present invention may be practiced in other embodiments that depart from these details and descriptions without departing from the spirit and scope of the invention. Certain embodiments will be described below with reference to the drawings wherein illustrative features are denoted by reference numerals.

The invention generally includes an apparatus for opening and closing the lid of a specimen vial, also herein referred to as a lid-actuator or lid-actuating device. The lid-actuator is generally adapted for use with automated laboratory equipment, for example, specimen auto sampling equipment, laboratory analytical testing equipment, product filling equipment, and the like. Additional features of the lid-actuator may further include a specimen vial ejection member, a vial catch tray, an input tray, and others, as is further described herein below. The lid-actuator apparatus can further be used for automated packaging of products, such as food products, powders, and the like.

Figure 1B:
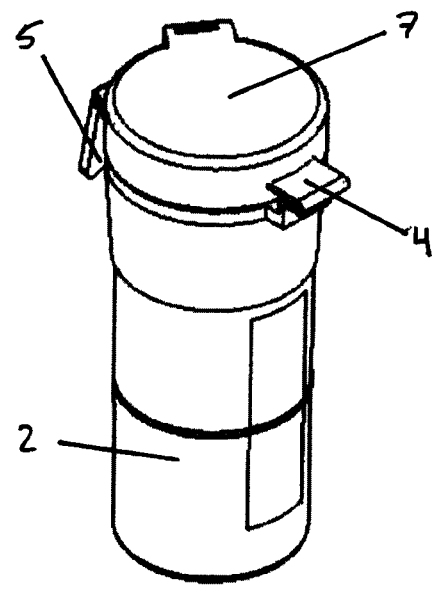
Figure 2A:
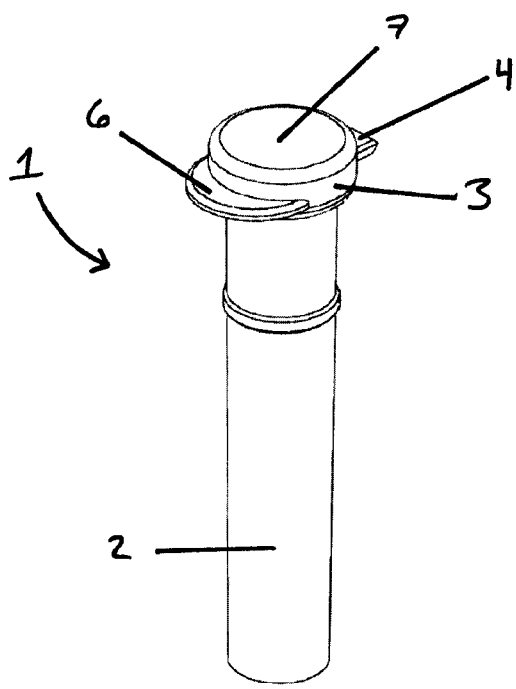
FIGS. 2(*a-b*) illustrate a perspective view of a typical saliva vial having a container body, a hinged lid, a rim tab.
Figure 2B:
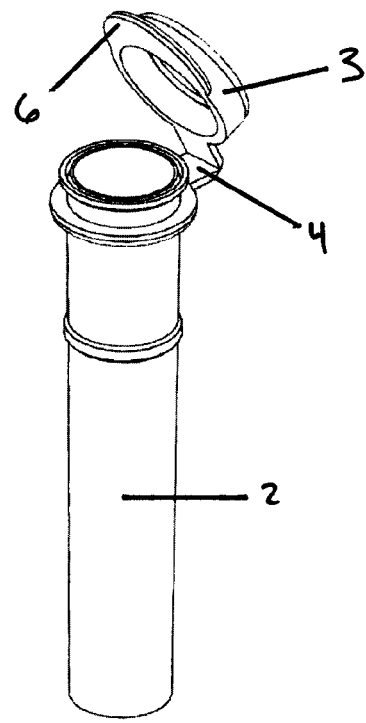

It is important to note that a variety of specimen vials are presently available and commonly used in the industry; the typical specimen vial 1, as represented in FIGS. 1-2, includes an elongated cylindrical tube forming the vial container 2, and a lid 3 connected to the vial container 2 at a lid-hinge 4. The lid 3 further includes one of: a hinged-tab 5 or a rim-tab 6 disposed on the lid 3 at a side opposite of the lid-hinge 4. Although the apparatus of the present invention as described in the following examples is designed to actuate these common testing vials, it should be understood by one having skill in the art that the invention can be used with generally any specimen vial, or other container having a container body and a lid hingedly disposed along a top portion of the container body. Accordingly, the following detailed examples are provided for illustrative purposes, and are not intended to limit the scope of the invention.

For purposes of this invention, the term "lid hinge" is defined as a folding hinge or other hinge characterized for rotational translation thereof which is disposed between a vial container and a vial lid, whereas the vial lid is attached to the vial container at the lid-hinge.

For purposes of this invention, the term "tab" is used herein to generally describe an elongated portion extending from a vial lid, including tabs referred to herein as "hinged-tab" and "rim-tab".

For purposes of this invention, the term "hinged tab" is defined as an elongated tab portion attached to a vial lid at a hinge. A hinged tab is adapted for rotational movement about an axis tangent to the lid at a point opposite of the lid-hinge. Referring to FIG. 1, the hinged tab 5, or hinged-tab, can further include a void for engaging a vial post 8 to securely maintain the vial lid in a closed position.

For purposes of this invention, the term "rim tab" is defined as a material portion which extends from the lid of a vial to form a rim or edge at a side opposite of a lid hinge; the material portion is fixedly disposed substantially coplanar with the vial lid.

For purposes of this invention, the term "linkage" is defined as a series of rigid links connected with joints to form a closed chain, or a series of closed chains. Each link has two or more joints, and the joints have various degrees of freedom to allow motion between the links.

For purposes of this invention, the term "lid actuator" is defined as an apparatus for engaging with the lid of a vial, the apparatus capable of mechanically translating the lid to an open position where an operation can be performed, and closing the lid of the vial.

For purposes of this invention, the term "tab engagement member" is defined as a mechanical component configured to engage with one of: a hinged-tab or a rim-tab; the tab engagement member is attached to a linkage for providing rotational force or leverage used to open the lid of a specimen vial. A lid-actuator may comprise one or more tab engagement members to facilitate engagement with one or more vial types or sizes.

For purposes of this invention, the term "open position" is used herein to describe a position of the lid relative to a closed position. When in operation, the lid-actuator opens the lid from a closed 0° horizontal position to a position greater than about 85° from horizontal, or a substantially vertical position. Once the lid is in a position greater than about 85° from horizontal, the lid is said to be in an open position, where an operation such as an aspiration can be performed with the contents of the vial container.

In a general embodiment of the invention, an apparatus for mechanical actuation of a vial lid is provided; the apparatus adapted to: open the lid of a specimen vial for providing access to the contents therein such that an aspiration or other operation can be performed, and close the lid of the specimen vial. The apparatus comprises a base; a vial alignment member extending vertically from the base; a tab engagement member for one or more of: aligning a vial, engaging a hinged tab, or engaging a rim tab; a motor, such as a stepper motor or servo motor; and a linkage for connecting the motor to the tab engagement member, wherein the linkage is adapted to provide an amount of force sufficient to open the lid of a vial.

One key feature of the invention includes a linkage for providing rotational force or leverage to a tab engagement member; the linkage is also herein referred to as a linkage assembly. The linkage generally includes a rotational arm comprising a first linkage member and a second linkage member. The first linkage member is adapted for attachment to the motor at a proximal end and extends radially outward to a distal end. The second linkage member is connected to the first linkage member at a first joint disposed on the distal end, the first joint including one of: a hinge, pin, bearing, or other attachment member adapted for rotational translation. The second linkage member is further connected to a third linkage member at a second joint disposed at the proximal end. The third linkage member, also termed a "lid support member", can be attached to the second linkage member at the second joint by any attachment member capable of providing rotational translation, such as a hinge, pin, bearing, or the like. The first linkage member, second linkage member, and lid support member are connected in series to form a mechanical linkage assembly. Additional linkage members can be incorporated to provide rotational movement along a desired path.

In one embodiment, a lid-actuator is adapted to open a vial having a hinged-tab, the lid actuator comprising: a base; a vial alignment member extending vertically from the base for aligning a vial in a substantially vertical position; a tab engagement member for engaging the vial at a hinged-tab; a motor; and a linkage for connecting the motor to the tab engagement member. The linkage further comprises a first linkage member attached to the motor at a proximal end and extending radially outward from the motor to a distal end, and a second linkage member attached to the first linkage member at the distal end. The second linkage member is further attached to a lid support member. The tab engagement member is disposed along said linkage for providing an amount of leverage sufficient to open the lid of said vial. In this embodiment, the tab engagement member is disposed along the second linkage member between the first joint and second joint.

The lid-actuator of the present invention does not require scoring of the vials or vial tape. The present invention provides a linkage capable of providing leverage to the tab opener such that the vials can be opened by the apparatus without additional preparation or scoring of tamper-evident tape. Additionally, when using a servo motor and a linkage as illustrated below, the momentum generated by the linkage assists in closing the vial tab when a closing motion is performed, therefore the present invention is capable of opening vials without scoring tamper-evident tape, and closing the vials completely to secure and re-engage the tab with the post of the vial.

The lid actuator can be designed and manufactured to perform opening and closing of vials of virtually any size. For example, a first lid actuator can be manufactured to operate with a 45 mL vial, and a second lid actuator can be manufactured to operate with a 90 mL vial. The operator can use the first lid actuator to sample a number of 45 mL vials, then simply remove the first lid actuator and replace with the second lid actuator to continue working with 90 mL vials. For simple removal, a lid actuator can be fitted with two holes and two screws driven through the two holes, the two screws securely mounting the lid actuator to an auto sampler or other machine. Additionally, the lid actuator can be configured to operate with saliva vials and other vials having a container body and hinged lid.

The tab engagement member is generally a rigid structure adapted to receive and engage one or more of: a hinged-tab or a rim-tab. The tab engagement member can comprise a rigid elongated portion having a slot disposed along the length thereof, such that a tab can become slideably engaged with the slot of the tab engagement member. The slot can further include a bottom surface and two side walls, wherein a tab can become captured between the two side walls of the slotted region within the tab engagement member. The tab engagement member can be positioned along the linkage at a point where an appropriate force can be applied to the tab of a vial during operation. A tab engagement member will generally be disposed along the second linkage member between the first joint and second joint for the purpose of opening vials having a vertically disposed hinged-tab. Similarly, the tab engagement member will generally be disposed along the lid support member between the second joint and third joint for the purpose of opening vials having a horizontally disposed rim-tab. It should be noted, however, that a slotted tab engagement member can be disposed along any portion of the linkage to obtain the result of engaging with a tab portion of a vial container.

The lid support member is a mechanical linkage member, and can further comprise a substantially planar surface adapted to engage with the top surface of a vial lid. The lid support member can further include an electrical switch for detecting the presence of a specimen vial. Where a specimen vial is detected by the electrical switch, the lid-actuator can begin operation to open the vial lid.

Lid-Actuator for a Sample Vial Having a Hinged-Tab

Figure 3:
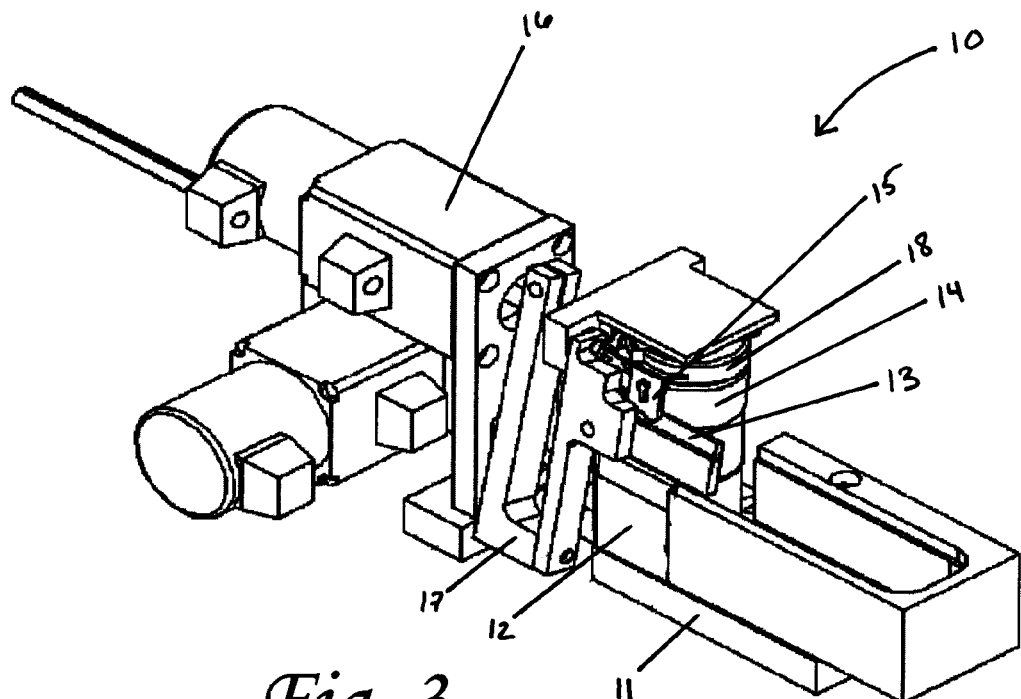
FIG. 3 is a perspective view of a lid-actuator according to one embodiment of the invention, the lid-actuator including a base, a linkage assembly, and a motor.
Figure 4:
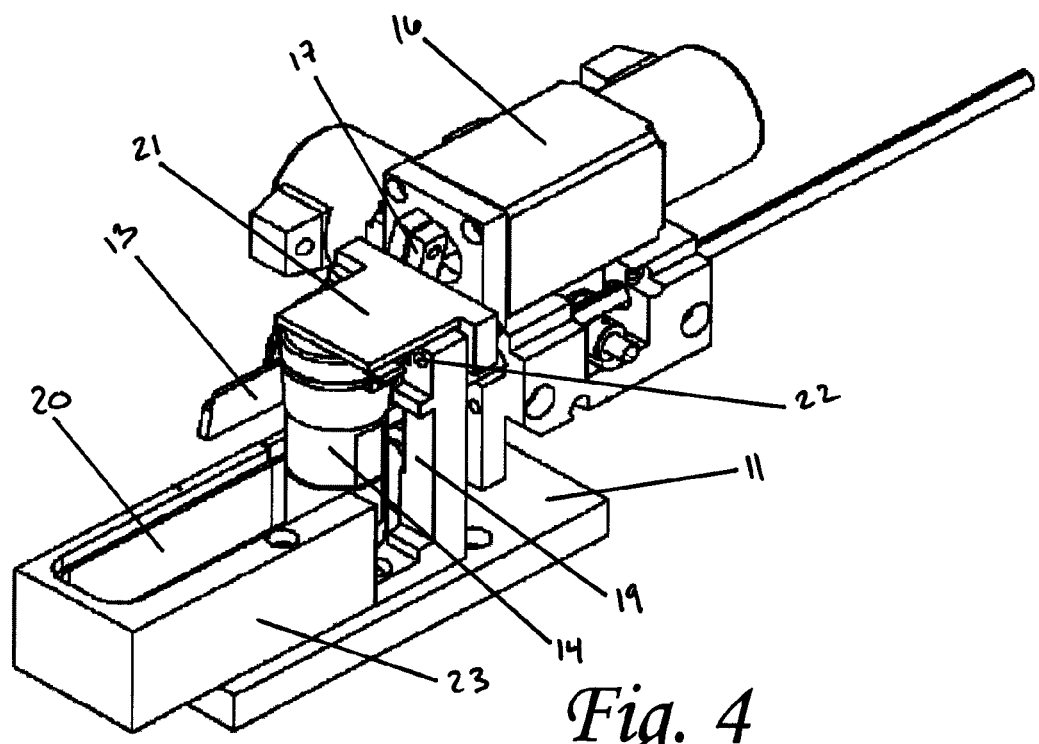
FIG. 4 is a perspective view of a lid-actuator according to one embodiment of the invention, the lid-actuator including a base, a linkage assembly, and a motor; the lid-actuator further including an ejection member.

Turning now to FIGS. 3-4, an apparatus for mechanical actuation of a vial lid is provided according to one embodiment of the invention. The apparatus comprising a base 11; a vial alignment member 12 extending vertically from the base 11; a tab engagement member 13 for one or more of: aligning a vial 14 or engaging a hinged-tab 15; a motor 16, such as a stepper motor or servo motor; and a linkage 17 for connecting the motor 16 to the tab engagement member 13, wherein the linkage 17 is adapted to provide an amount of leverage sufficient to open the hinged-tab 15 and lid 18 of a vial 14. The linkage 17 can be connected to the motor 16 directly, or at a gear or pulley. The linkage is therefore rotationally engaged with the motor at a rotational axis, the rotational axis extending outwardly at a point where the linkage is connected to the motor, gear, or pulley.

The base 11, vial alignment member 12, rear-wall 19, and lid support member 21 of the lid actuator cooperate to form a substantially captivating enclosure for receiving a specimen vial 14. While maintained in the enclosure, the vial 14 remains in an upright vertical position and the hinged tab 15 of the vial is engaged by the tab engagement member 13. The tab engagement member may further include a tab slot for receiving and retaining the tab during operation of the lid actuator. The lid actuator further comprises a rear wall 19 extending vertically from the base, the rear wall including a joint post and third joint 22 for connecting the lid support member 21 of the linkage assembly.

A specimen vial catch tray 23 is further provided, the catch tray including an elongated member having a cavity 20 disposed longitudinally thereon. The cavity 20 includes an interior width larger than the diameter of the testing vial for maintaining one or more specimen vials in an upright orientation. The catch tray 23, sample enclosure and contained vial 14, and linkage 17 can be disposed along the rotational axis of the lid actuator, such that the lid actuator 10 is adapted to rotationally open the lid of the vial and close the lid of the vial.

The linkage can be driven by any motor known in the art, preferably a servo motor or stepper motor. The linkage can be attached directly to the motor, or alternatively the linkage can be attached to the motor by one or more gears or a pulley. Where a pulley assembly is used, the linkage can be engaged with the motor using a belt or a chain.

The lid actuator can further include an ejection member. The ejection member generally includes an elongated rod 24 disposed along the rotational axis 25 of the lid actuator 10, and a translation mechanism for translating the elongated rod 24 in a direction for engaging a specimen vial and ejecting the vial from the enclosure to the cavity 20 of the catch tray 23. Although a rack and pinion system 26 is illustrated in FIGS. 5-6, it will be understood that the elongated rod can be driven by any translation mechanism such as: a rack and pinion, pneumatic actuator, hydraulic actuator, linear servo motor, manually operated guide, retractable linkage, jointing arm, or the like.

The ejection member comprises an elongated rod, or rack, connected to a gear, or pinion 27, the pinion 27 is driven by a motor 30 such as a servo motor, stepper motor, or the like. After performing an operation, the lid actuator can close the lid of the specimen vial before translating the ejection member to engage and eject the vial into the catch tray before retracting to a home position. In this embodiment, the rear wall of the lid actuator includes an aperture 29, the elongated rod 24 is adapted to translate linearly along the rotational axis 25 of the lid actuator 10, entering the enclosure at the aperture 29 of the rear wall 19, and engaging the specimen vial.

The lid actuator can further comprise an input tray (not illustrated) for maintaining a plurality of vials in a substantially upright position. The input tray can include a recessed portion having a width greater than a diameter of the vials tested.

Figure 5:
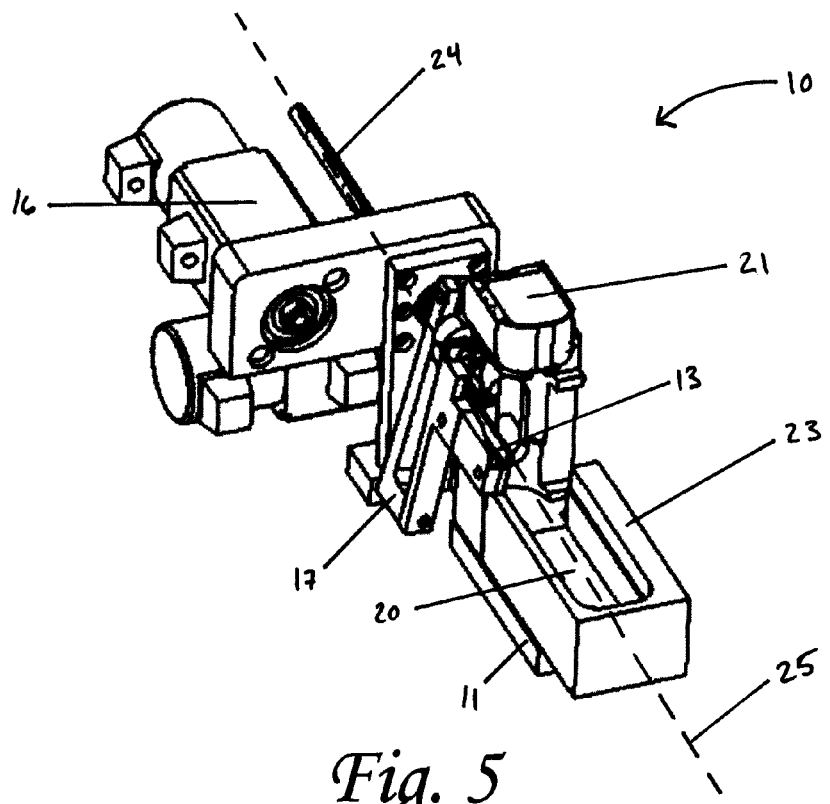
FIG. 5 is a perspective view of a lid-actuator according to one embodiment of the invention, the lid-actuator including a base, a linkage assembly, and a motor.
Figure 6:
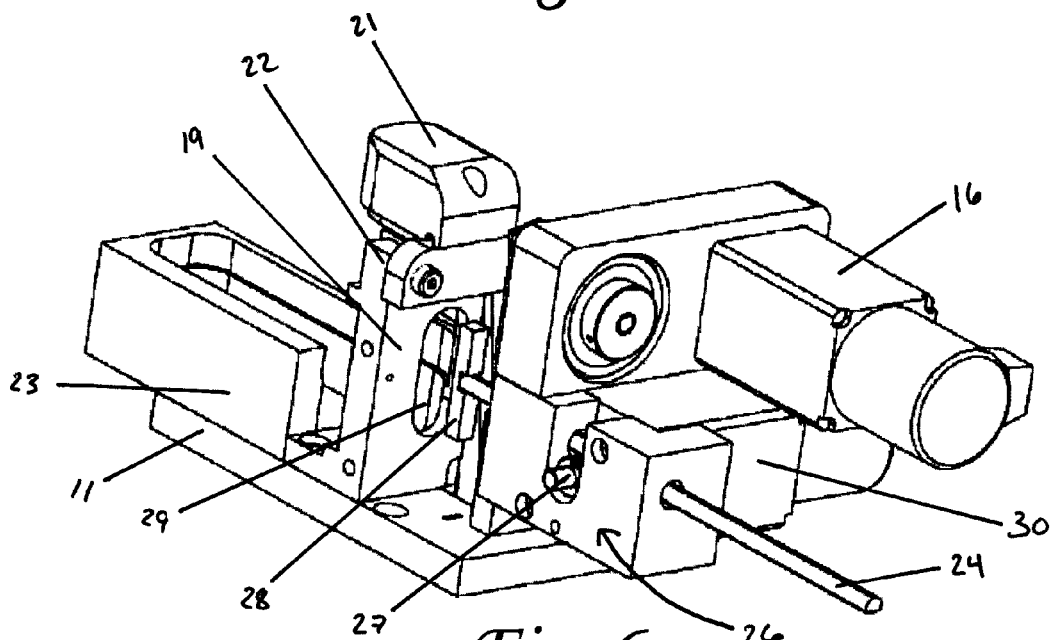
FIG. 6 is a perspective view of a lid-actuator according to one embodiment of the invention, the lid-actuator including a base, a linkage assembly, and a motor.

FIGS. 5-6 illustrate the lid actuator according to an embodiment of the invention. The lid actuator includes a rear wall 19 extending vertically from the base 11, the rear wall 19 further comprising an aperture 29 for penetration by the ejection member 24. The aperture 29 is disposed along the rotational axis 25 of the lid actuator 10 such that the elongated rod 24 is capable of penetrating the aperture 29 to engage and eject a sample vial from the enclosure. The elongated rod 24 may further comprise a vial engagement pad 28 attached to the elongated rod 24 at a first end, such that a specimen vial can become engaged by the elongated rod at a vial engagement pad 28.

Figure 7:
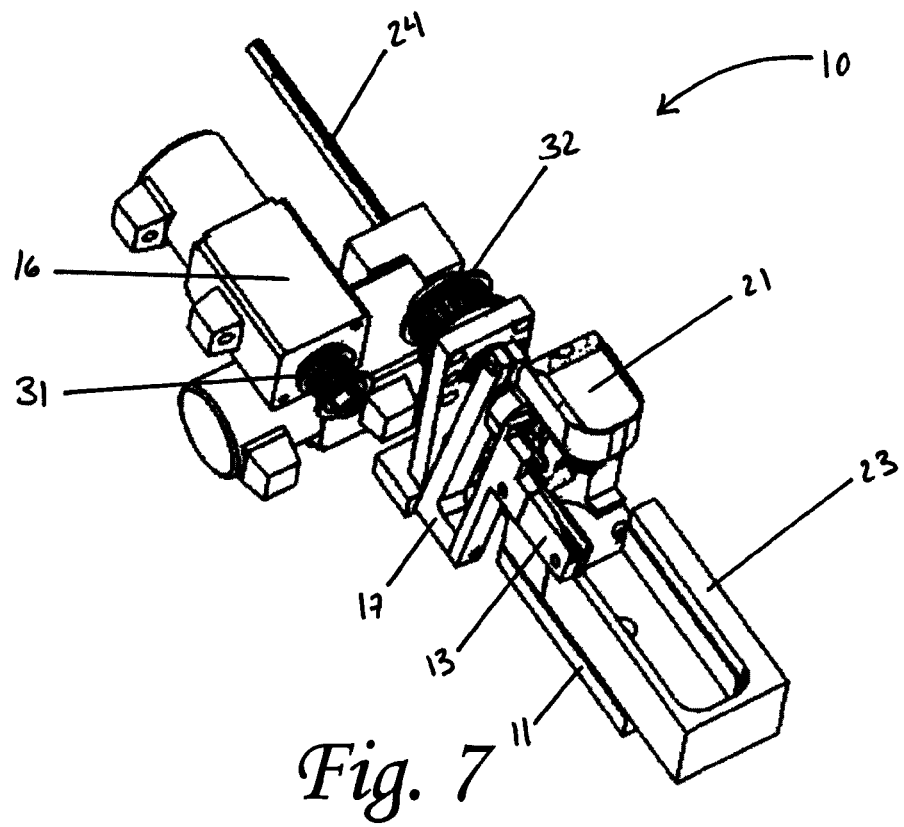
FIG. 7 is a perspective view of a lid-actuator according to one embodiment of the invention, the lid-actuator including a base, a linkage assembly, and a motor; the lid-actuator further including a first gear and a second gear.

FIG. 7 further illustrates the lid actuator according to an embodiment of the invention, the lid actuator 10 including a motor 16 having a first gear 31, and a linkage 17 attached at a second gear 32. One having ordinary skill in the art will recognize that the first gear 31 can be connected to the second gear 32 by any of: a gear assembly, band, or chain. Upon rotational movement, the motor is adapted to rotationally translate the linkage assembly, thereby applying leverage to the tab and opening the lid of a specimen vial.

Figure 8:
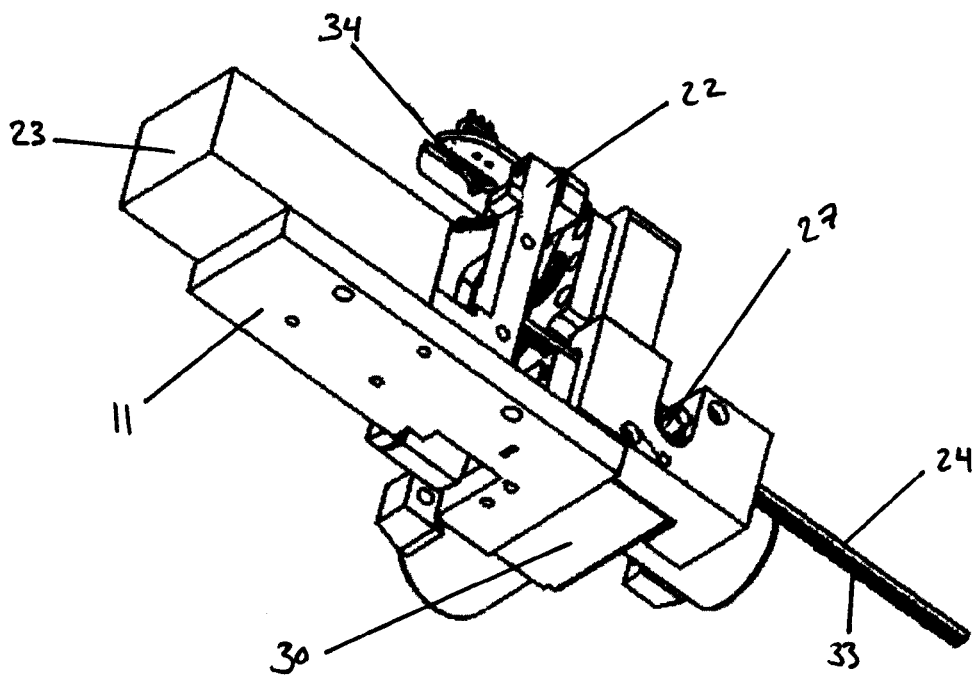
FIG. 8 is a perspective view of a lid-actuator according to one embodiment of the invention, the lid-actuator including a base, a linkage assembly, and a motor; the lid-actuator further including a vial indicator switch.
Figure 9A:
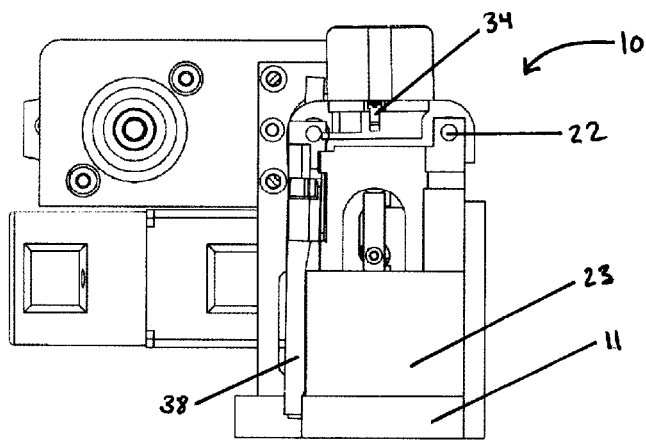
FIGS. 9 (*a-f*) illustrate a front view of the lid-actuator according to an embodiment of the invention, each successive figure illustrating a series function of the lid-actuator.
Figure 9B:
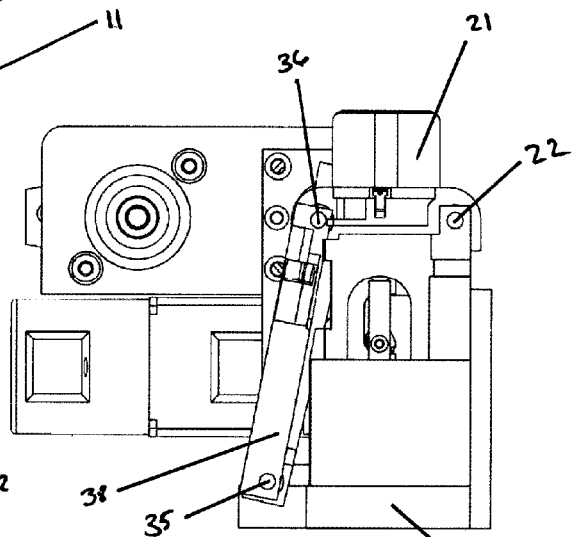
Figure 9C:
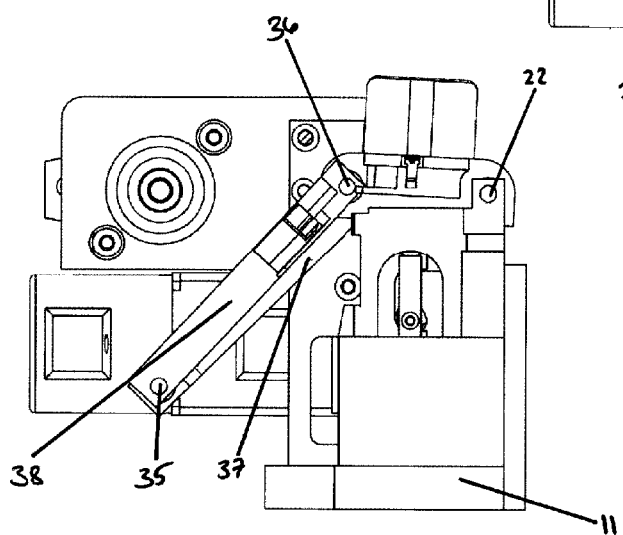
Figure 9D:
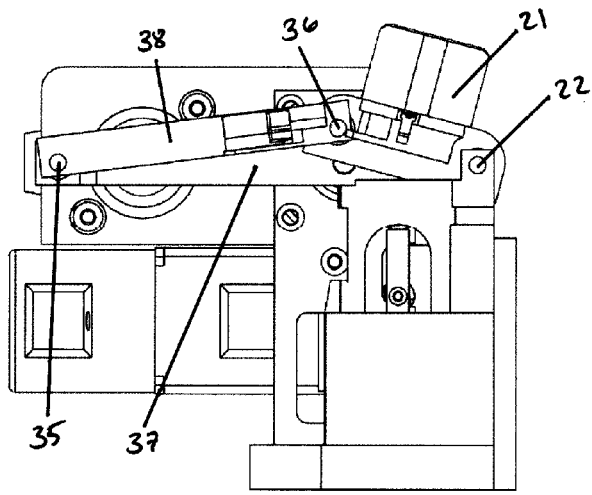
Figure 9E:
Figure 9F:
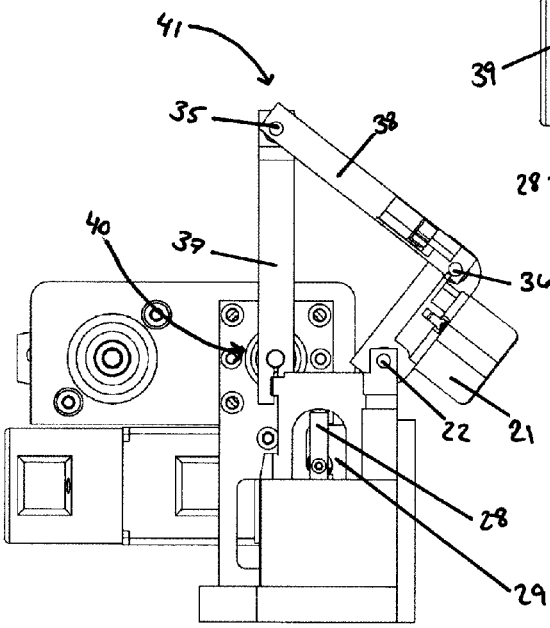

FIG. 8 illustrates the assembly according to an embodiment of the invention, the assembly including an ejection member having an elongated rod 24, or rack, driven by a gear 27, or pinion, the pinion driven by a motor 30. The elongated rod 24 further includes a series of teeth 33 disposed along a bottom portion of the rod, the teeth are adapted to engage the pinion for translational movement. The lid-actuator further includes an electrical switch 34 disposed on the bottom surface of the lid support member, the electrical switch is configured to detect the presence of a specimen vial.

FIGS. 9 (a-g) illustrate the rotational movement of the lid actuator described in FIGS. 3-8. The lid actuator includes a linkage assembly driven by a motor, the linkage including a tab engagement member for engaging the tab of a specimen vial. As the motor rotates, the linkage assembly is rotationally translated, and the tab is disengaged from the post of the specimen vial. As the linkage continues to rotationally translate, the lid of the vial is opened until it reaches an open position as illustrated in FIG. 9f. The motor can then reverse direction to allow the linkage assembly to close the vial lid, and re-engage the tab with the post of the vial container.

The linkage assembly can include a first linkage member 37 connected to the motor at a proximal end 40 and extending radially outward to a distal end. The first linkage member 37 includes a first joint 35 disposed at the distal end 41. A second linkage member 38 is connected to the first linkage member 37 at the distal end by the first joint 35 and extends radially inward towards the rotational axis of the lid-actuator. The second linkage member 38 can further be attached to a third linkage member 21, or lid support member, at a second joint 36. The third linkage member is further attached to the rear-wall 19 of the vial enclosure at a third joint 22. The first linkage member 37, first joint 35, second linkage member 38, second joint 36, lid support member 21, and third joint 22 are collectively referred to as the mechanical linkage assembly.

Figure 10:
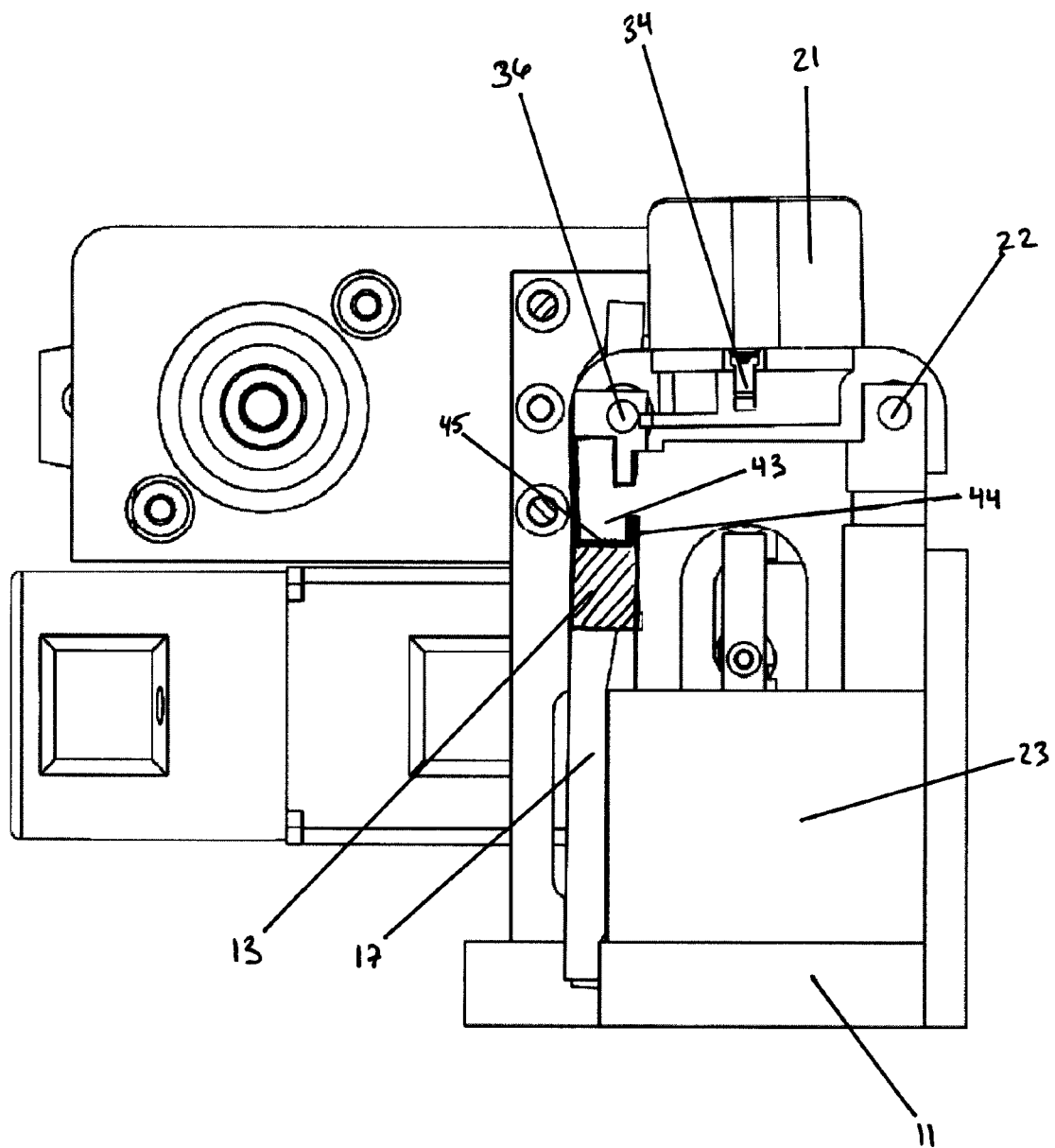
FIG. 10 is a front view of a lid-actuator according to an embodiment of the invention, the lid-actuator including a linkage and a tab engagement member, the tab engagement member is configured to engage a hinged tab of a specimen vial.

FIG. 10 illustrates a lid-actuator according to an embodiment of the invention wherein the lid-actuator is adapted to engage a specimen vial having a hinged-tab. The lid actuator comprises a base 11; a vial alignment member extending vertically from the base; a tab engagement member 13 for aligning a vial and engaging a hinged-tab; a motor; and a linkage 17 for connecting the motor to the tab engagement member, wherein the linkage is adapted to provide an amount of leverage sufficient to open the hinged-tab and lid of a vial. The tab engagement member 13 further comprises a slot 43 having a bottom surface 45 and a side wall 44 configured to engage a hinged-tab.

Lid-Actuator for a Sample Vial Having a Rim-Tab

Figure 11:
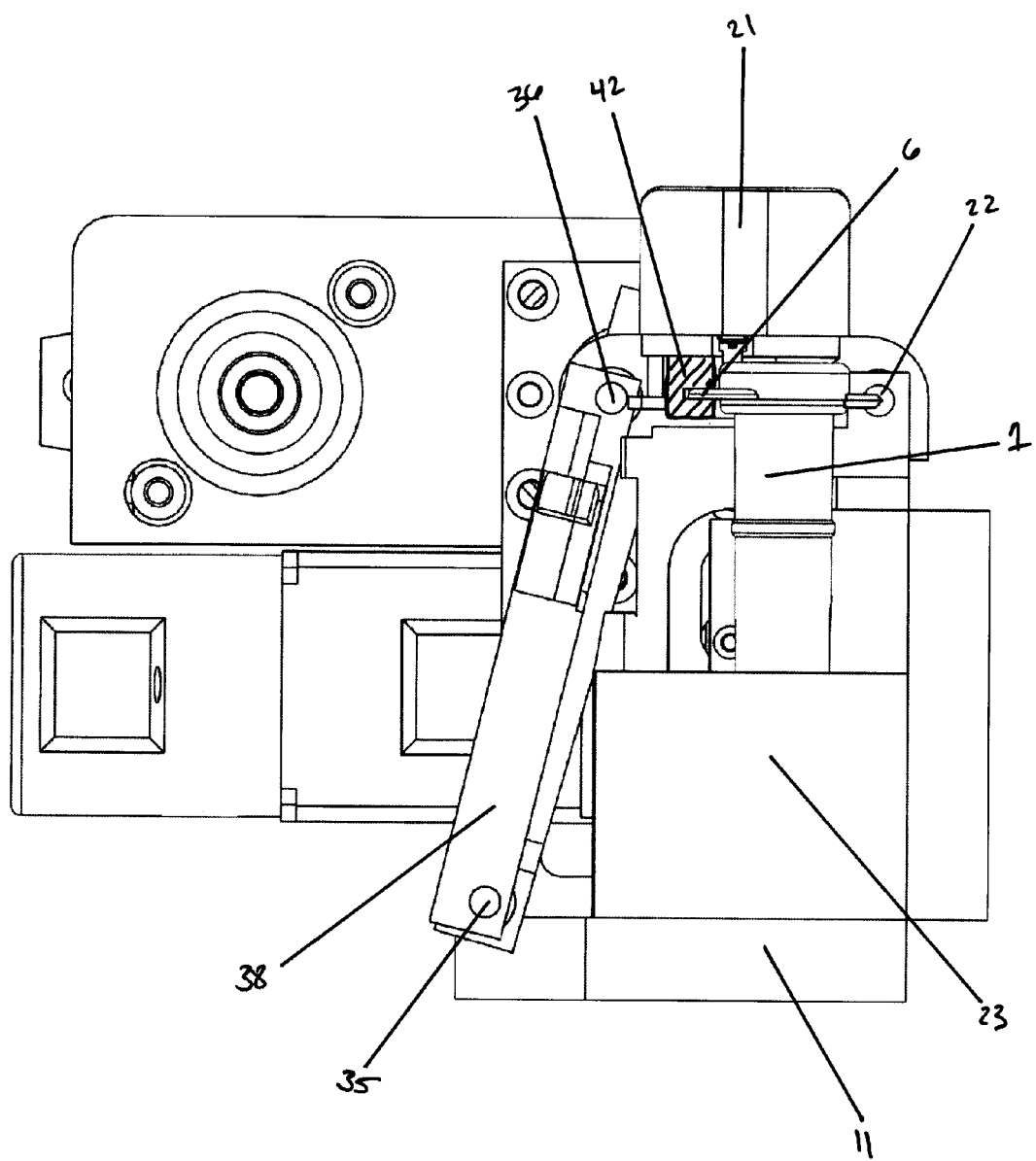
FIG. 11 is a front view of a lid-actuator according to an embodiment of the invention, the lid-actuator including a linkage and a tab engagement member, the tab engagement member is configured to engage a rim tab of a saliva vial.

In another embodiment as illustrated by FIG. 11, a lid-actuator is adapted to open a saliva vial having a rim-tab, the lid actuator comprising: a base 11; a vial alignment member extending vertically from the base for aligning a vial in a substantially vertical position; a tab engagement member 42 for engaging the vial at a rim-tab 6; a motor; and a linkage for connecting the motor to the tab engagement member. The linkage further comprises a first linkage member attached to the motor at a proximal end and extending radially outward from the motor to a distal end, and a second linkage member 38 attached to the first linkage member at the distal end. The second linkage member is further attached to a lid support member 21 and the tab engagement member 42 is disposed along the lid support member 21 for providing an amount of leverage sufficient to open the lid of the vial 1. In this embodiment, the tab engagement member 42 is disposed along the third linkage member 21, or lid support member, between the second joint 36 and a third joint 22.

In another embodiment, the lid-actuator comprises a first tab engagement member disposed along the second linkage member between the first joint and second joint, and a second tab engagement member disposed along the lid support member between the second joint and third joint. The second tab engagement member can be removably attached, such that the lid actuator is adapted to open saliva vials with the second tab engagement member attached thereto, and the lid actuator can further open another vial type, such as a 45 mL vial, when the second tab engagement member is removed. The second tab engagement member can be attached by a friction fit, clasp, pin, screw, or the like.

The above examples are set forth for illustrative purposes and are not intended to limit the spirit and scope of the invention. One having skill in the art will recognize that deviations from the aforementioned examples can be created which substantially perform the same tasks and obtain similar results.

We claim:

1. An apparatus for mechanical actuation of a vial lid between an open and closed state, comprising:
a base,
a vial alignment member extending vertically from said base for aligning a vial in a substantially vertical position,
a tab engagement member for engaging said vial at a tab,
a motor, and
a linkage for connecting the motor to the tab engagement member,
said linkage further comprising a first linkage member attached to said motor at a proximal end and extending radially outward from said motor to a distal end, and a second linkage member attached to said first linkage member at said distal end, said second linkage member further attached to a lid support member,
wherein said tab engagement member is disposed along said linkage for providing an amount of leverage sufficient to open a tab and a lid of said vial;
wherein said motor and linkage are adapted to close the lid of the vial; and
wherein said motor and linkage are adapted to close the tab of the vial.

2. The apparatus of claim 1, wherein said apparatus is adapted to engage said tab with said vial in a lid-closing rotation.

3. The apparatus of claim 1, wherein said second linkage member is attached to said first linkage member at a first joint.

4. The apparatus of claim 3, said first joint comprising a pin disposed along an axis perpendicular to each of said first and second linkage members, wherein said first and second linkage members are adapted for rotational movement about said axis.

5. The apparatus of claim 1, said apparatus further comprising a lid support member for engaging one of the top surface or bottom surfaces of said vial lid, said lid support member further attached to said second linkage member at a second joint.

6. The apparatus of claim 5, further comprising a rear wall extending vertically from said base, said rear wall comprising a third joint, wherein said lid support member is connected to said rear wall at said third joint.

7. The apparatus of claim 1, wherein said motor is one of: a servo motor, or a stepper motor.

8. The apparatus of claim 1, further comprising a gear assembly, wherein said first linkage member is connected to said motor at said gear assembly.

9. The apparatus of claim 1, further comprising a catch tray attached to said base, said catch tray adapted to receive said vial and maintain said vial in a substantially vertical orientation.

10. The apparatus of claim 9, wherein said catch tray is adapted to receive and maintain a plurality of vials in a substantially vertical orientation.

11. The apparatus of claim 9, further comprising an ejection member for ejecting said vial into said catch tray.

12. The apparatus of claim 11, said ejection member comprising an elongated rod.

13. The apparatus of claim 12, wherein said ejection member is translated by one of: a rack and pinion, pneumatic actuator, linear servo motor, manually operated guide, retractable linkage, or jointing arm.

14. The apparatus of claim 13, said ejection member further comprising a vial engagement pad, said vial engagement pad fixedly attached to said elongated rod at a first end.

15. An apparatus for opening and closing a lid of a specimen vial, comprising:
a motor engaged with a linkage arm, the linkage arm comprising a lid support member and a tab engagement member;
an ejection member adapted to eject a vial from the lid opening device;

wherein the linkage arm is adapted to engage the tab engagement member and translate the tab engagement member to unlock a tab from a vial, use leverage to rotationally open a lid of the vial at the lid support member, close the lid, and lock the tab with the vial;

and wherein the ejection member is adapted to eject the vial from the apparatus.

16. An apparatus for opening and closing a lid of a specimen vial, comprising:

a motor engaged with a linkage arm, the linkage arm comprising a lid support member and a tab engagement member;

wherein the linkage arm is adapted rotationally open a lid of the vial at the lid support member and subsequently close the lid of the vial.

17. The apparatus of claim 16, wherein the linkage arm is adapted to engage the tab engagement member and translate the tab engagement member to unlock a tab from a vial, use leverage to rotationally open a lid of the vial at the lid support member, close the lid, and lock the tab with the vial.

* * * * *